(12) United States Patent
Sela et al.

(10) Patent No.: US 10,925,687 B2
(45) Date of Patent: Feb. 23, 2021

(54) SYSTEM AND METHOD FOR OPTICAL AXIS CALIBRATION

(71) Applicants: Gal Sela, Toronto (CA); Kamyar Abhari, Toronto (CA)

(72) Inventors: Gal Sela, Toronto (CA); Kamyar Abhari, Toronto (CA)

(73) Assignee: Synaptive Medical Inc., Toronto (CA)

( * ) Notice: Subject to any disclaimer, the term of this patent is extended or adjusted under 35 U.S.C. 154(b) by 0 days.

(21) Appl. No.: 16/510,040

(22) Filed: Jul. 12, 2019

(65) Prior Publication Data

US 2021/0007825 A1 Jan. 14, 2021

(51) Int. Cl.
*G06T 7/00* (2017.01)
*A61B 90/00* (2016.01)
*A61B 34/20* (2016.01)
*G06T 7/80* (2017.01)

(52) U.S. Cl.
CPC .......... *A61B 90/361* (2016.02); *A61B 34/20* (2016.02); *G06T 7/80* (2017.01); *A61B 2034/2057* (2016.02); *A61B 2034/2065* (2016.02)

(58) Field of Classification Search
CPC .......... A61B 90/361; A61B 34/20; A61B 2034/2057; A61B 2034/2065; G06T 7/80
See application file for complete search history.

(56) References Cited

U.S. PATENT DOCUMENTS

| 9,068,820 | B2 | 6/2015 | Kosmecki et al. | |
|---|---|---|---|---|
| 10,134,133 | B2 | 11/2018 | Zhao et al. | |
| 2004/0128102 | A1* | 7/2004 | Petty | G01S 5/163 702/150 |
| 2012/0253201 | A1* | 10/2012 | Reinhold | H04N 13/254 600/473 |
| 2013/0315440 | A1* | 11/2013 | Frank | G06K 9/3275 382/103 |
| 2014/0100694 | A1* | 4/2014 | Rueckl | B25J 9/1692 700/254 |
| 2016/0048953 | A1* | 2/2016 | Zhao | G06K 9/4671 382/103 |
| 2016/0288332 | A1* | 10/2016 | Motoyoshi | B25J 9/1697 |
| 2017/0239491 | A1* | 8/2017 | Xia | A61B 5/004 |
| 2017/0337700 | A1* | 11/2017 | Wilson | G06K 9/6201 |
| 2017/0374360 | A1* | 12/2017 | Kranski | G06T 7/85 |
| 2018/0004188 | A1* | 1/2018 | Yamaguchi | B25J 13/02 |
| 2019/0364206 | A1* | 11/2019 | Dal Mutto | G06T 7/85 |
| 2020/0005448 | A1* | 1/2020 | Subramanian | G06F 30/17 |

* cited by examiner

*Primary Examiner* — Zhihan Zhou
(74) *Attorney, Agent, or Firm* — Rowand LLP

(57) ABSTRACT

A method for calibrating an optical axis of a camera mounted to a movable structure is disclosed. The method includes: for each of two or more standoff distances for the camera: capture, using the camera, image data of a target marker while the movable structure is undergoing rotation about a fixed axis, the target marker being a grid of squares each including unique detectable features; determine a respective center of rotation based on the captured image data; determine a first axis which goes through the centers of rotation; and determine a transform between the first axis and a second axis through the center of output image of the camera.

12 Claims, 8 Drawing Sheets

SYSTEM AND METHOD FOR OPTICAL AXIS CALIBRATION

TECHNICAL FIELD

The present disclosure relates to medical imaging and, in particular, to optical imaging systems suitable for use in image-guided medical procedures.

BACKGROUND

Digital microscopes support advanced visualization during medical procedures. For example, digital surgical microscopes provide magnified views of anatomical structures during a surgery. Digital microscopes use optics and digital (e.g. CCD-based) cameras to capture images in real-time and output the images to displays for viewing by a surgeon, operator, etc.

In image-guided medical applications, such as surgery or diagnostic imaging, accurate three-dimensional (3-D) visualization of patient anatomy and surgical tools is crucial. A medical navigation system is often used to support image-guided surgery. In an exemplary medical navigation system, an optical imaging system may be provided for generating 3-D views of a surgical site. A positioning system, such as a mechanical arm, may support the optical imaging system and facilitate maneuvering the optical imaging system to an appropriate position and orientation to maintain alignment with a viewing target. One source of problems for a medical navigation system is misalignment between a mechanical axis of the optical imaging system and its optical axis. In surgical microscope applications, even a small misalignment of the axes may be unacceptable. Accordingly, it is desirable to provide a solution for reliably calibrating the optical axis of a surgical microscope.

BRIEF DESCRIPTION OF DRAWINGS

Reference will now be made, by way of example, to the accompanying drawings which show example embodiments of the present application and in which.

Like reference numerals are used in the drawings to denote like elements and features.

DETAILED DESCRIPTION OF EXAMPLE EMBODIMENTS

Figure 1:
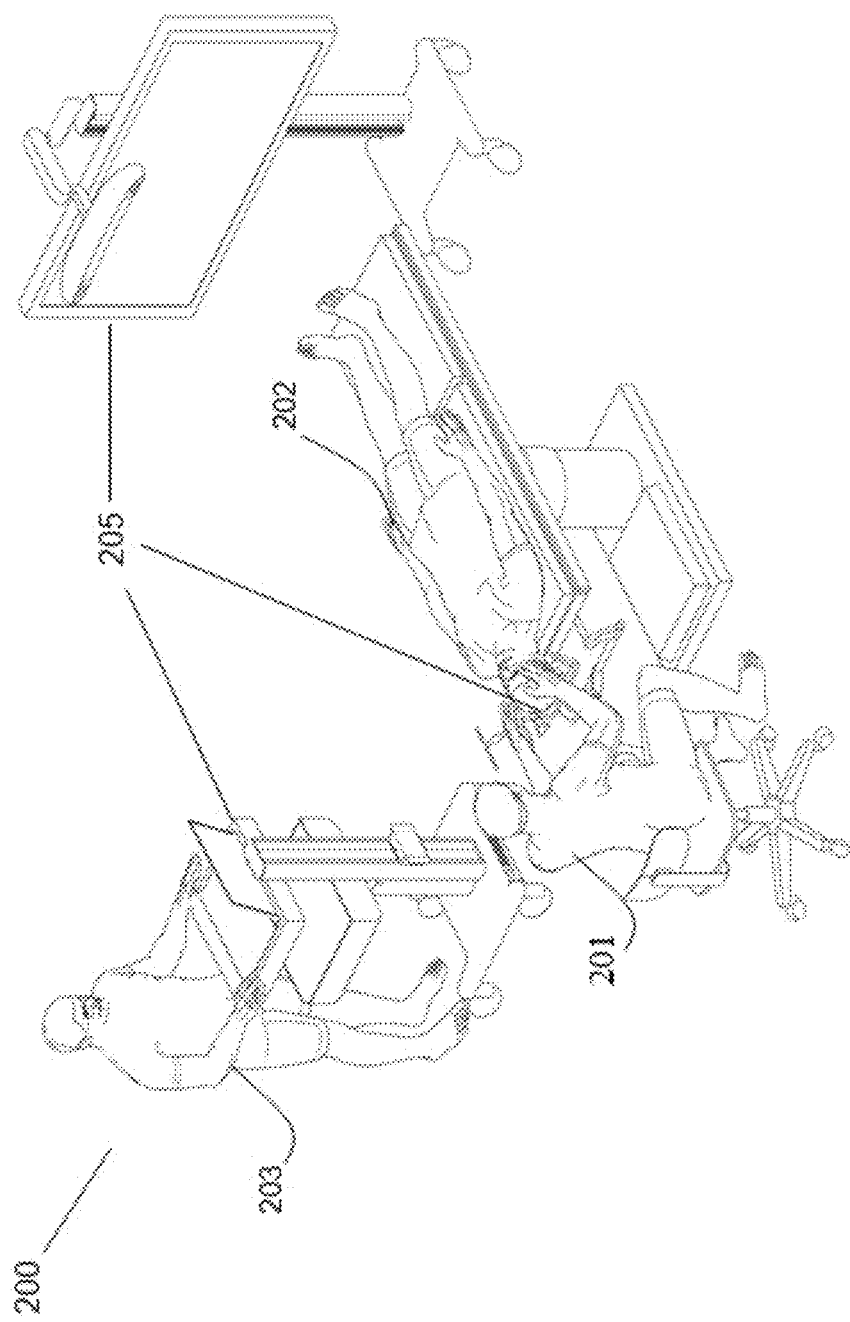
FIG. 1 shows an example navigation system to support image-guided surgery.

In one aspect, the present disclosure describes a method for calibrating a camera mounted to a movable structure. The method includes: for each of two or more standoff distances for the camera: capture, using the camera, image data of a target marker while the movable structure is undergoing rotation about a fixed axis, the target marker being a grid of squares each including unique detectable features; determine a respective center of rotation based on the captured image data; determine a first axis which goes through the centers of rotation; and determine a transform between the first axis and a second axis through the center of the camera screen.

In some implementations, the movable structure may be a robotic arm, and the robotic arm may be rotatable about a fixed wrist joint.

In some implementations, the image data may comprise video of the target marker.

In some implementations, the method may further comprise: processing the video to identify unique IDs associated with the different features of the grid squares; and identifying patterns marked by the unique IDs in the video frames as a result of rotation of the movable structure.

In some implementations, the patterns may comprise a plurality of concentric tracking circles marked by the unique IDs.

In some implementations, the two or more standoff distances may be selected based on minimum and maximum focal lengths of optics of the camera.

In some implementations, the two or more standoff distances may be selected from a range between 25 centimeters to 55 centimeters.

In some implementations, the method may further comprise validating the calibration, wherein the validation is done by performing a rotation of the movable structure about the determined first axis at a standoff distance that is different from the two or more standoff distances and determining whether the center of rotation is very close to the center of the camera screen.

In some implementations, the validation may further comprise measuring the distance in pixels between the center of the camera screen and the center of optical axis rotation.

In some implementations, the target marker may comprise an Aruco marker.

In another aspect, the present disclosure describes an optical imaging system for imaging a target during a medical procedure. The optimal imaging system includes a movable arm, a camera mounted on the movable arm, the camera capturing a first image of the target, and a processing unit for calibrating the camera. The processing unit is configured to: for each of two or more standoff distances for the camera: capture, using the camera, image data of a target marker while the movable structure is undergoing rotation about a fixed axis, the target marker being a grid of squares each including unique detectable features; determine a respective center of rotation based on the captured image data; determine a first axis which goes through the centers of rotation; and determine a transform between the first axis and a second axis through the center of the camera screen.

Other example embodiments of the present disclosure will be apparent to those of ordinary skill in the art from a review of the following detailed descriptions in conjunction with the drawings.

In the present application, the phrase "access port" is intended to refer to a cannula, a conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

In the present application, the term "intraoperative" is intended to refer to an action, process, method, event, or step that occurs or is carried out during at least a portion of a medical procedure. Intraoperative, as defined herein, is not limited to surgical procedures, and may refer to other types of medical procedures, such as diagnostic and therapeutic procedures.

In the present application, the term "and/or" is intended to cover all possible combinations and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

The present application provides a calibration tool for a camera that is mounted to a movable structure. In particular, the disclosed methods facilitate calibrating an optical axis of a camera that is mounted to a positioning apparatus, such as a controllable robotic arm, of a medical navigation system. The calibration tool can be used to determine the camera's orientation relative to an axis of rotation, and compensate for any mounting variability of the camera on the positioning apparatus. Using a target marker containing unique detectable features, the positioning apparatus can be calibrated using optical information. Specifically, while the positioning apparatus is performing rotations, video data of the target marker is recorded and processed to find a center of rotation. The optical axis can be generated by determining an offset between how far off the center of rotation is from the center of the camera screen.

Reference is first made to FIG. 1, which shows an example navigation system 200. The example navigation system 200 may be used to support image-guided surgery. As shown in FIG. 1, a surgeon 201 conducts a surgery on a patient 202 in an operating room environment. A medical navigation system 205 may include an equipment tower, tracking system, displays, and tracked instruments to assist the surgeon 201 during a procedure. An operator 203 may also be present to operate, control, and provide assistance for the medical navigation system 205.

Figure 2:
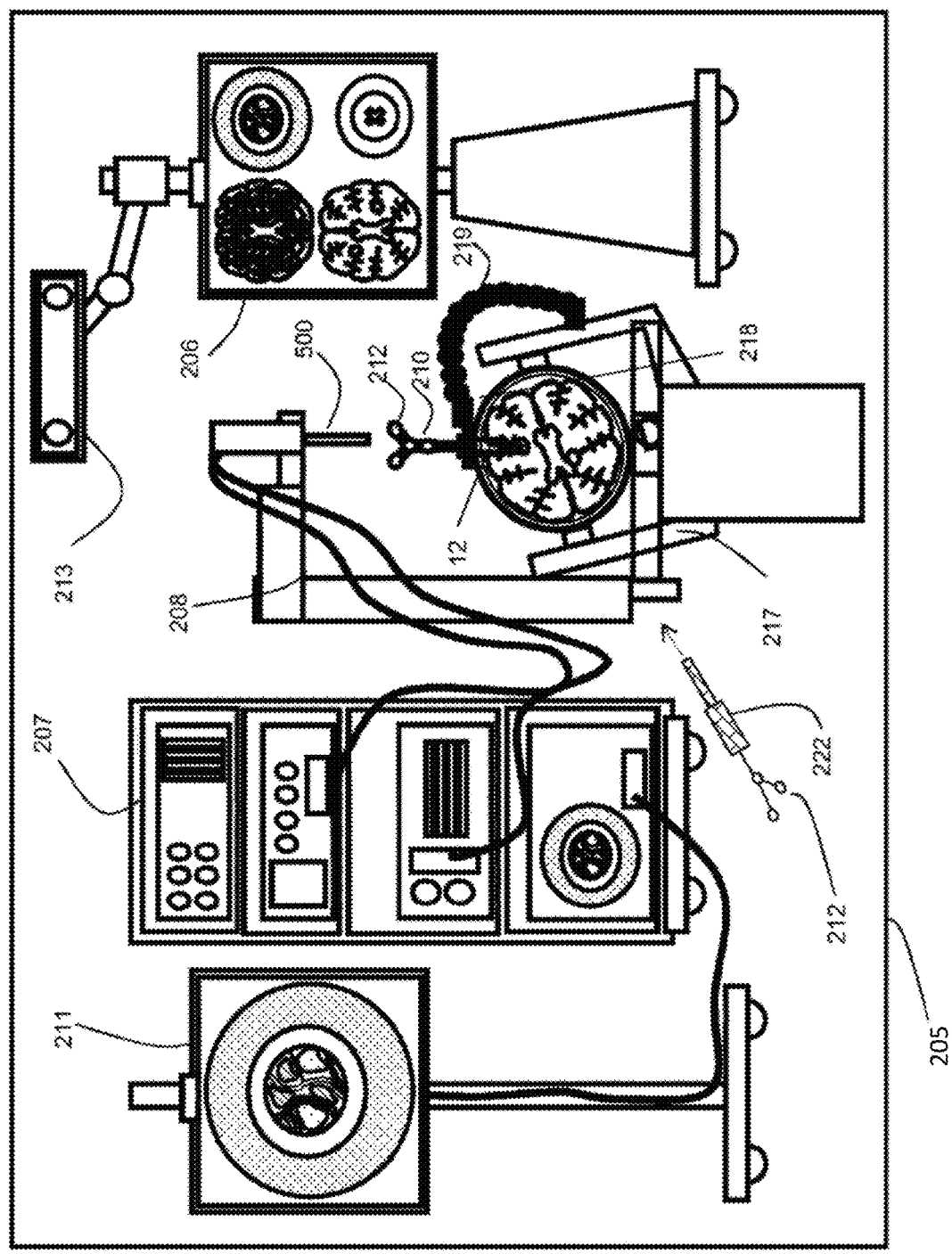
FIG. 2 illustrates components of an example navigation system.

FIG. 2 shows components of an example medical navigation system 205. The disclosed augmented optical imaging system may be used in the context of the medical navigation system 205. The medical navigation system 205 may include one or more displays 206, 211 for displaying video images, an equipment tower 207, and a positioning system 208, such as a medical arm, which may support an optical imaging system 500. One or more of the displays 206, 211 may include a touch-sensitive display for receiving touch input. The equipment tower 207 may be mounted on a frame, such as a rack or cart, and may contain a power supply and a computer/controller that may execute planning software, navigation software, and/or other software to manage the positioning system 208. In some examples, the equipment tower 207 may be a single tower configuration operating with dual displays 206, 211; however, other configurations (e.g. dual tower, single display etc.) may also exist. The equipment tower 207 may also be configured with a universal power supply (UPS) to provide for emergency power, in addition to a regular AC adapter power supply.

A portion of the patient's anatomy may be held in place by a holder. For example, as shown in FIG. 2, the patient's head and brain may be held in place by a head holder 217. An access port 12 and associated introducer 210 may be inserted into the head, to provide access to a surgical site in the head. The optical imaging system 500 may be used to view down the access port 12 at a sufficient magnification to allow for enhanced visibility down the access port 12. The output of the optical imaging system 500 may be received by one or more computers or controllers to generate a view that may be depicted on a visual display (e.g. one or more displays 206, 211).

In some examples, the navigation system 205 may include a tracked pointer 222. The tracked pointer 222, which may include markers 212 to enable tracking by a tracking camera 213, may be used to identify points (e.g. fiducial points) on a patient. An operator, typically a nurse or the surgeon 201, may use the tracked pointer 222 to identify the location of points on the patient 202, in order to register the location of selected points on the patient 202 in the navigation system 205. In some embodiments, a guided robotic system with closed loop control may be used as a proxy for human interaction. Guidance to the robotic system may be provided by any combination of input sources such as image analysis, tracking of objects in the operating room using markers placed on various objects of interest, or any other suitable robotic system guidance techniques.

Fiducial markers 212 may be connected to the introducer 210 for tracking by the tracking camera 213, which may provide positional information of the introducer 210 from the navigation system 205. In some examples, the fiducial markers 212 may be alternatively or additionally attached to the access port 12. In some examples, the tracking camera 213 may be a 3-D infrared optical tracking stereo camera. In some other examples, the tracking camera 213 may be an electromagnetic system (not shown), such as a field transmitter that may use one or more receiver coils located on the tool(s) to be tracked. A known profile of the electromagnetic field and known position of receiver coil(s) relative to each other may be used to infer the location of the tracked tool(s) using the induced signals and their phases in each of the receiver coils.

Location data of the positioning system 208 and/or access port 12 may be determined by the tracking camera 213 by detection of the fiducial markers 212 placed on or otherwise in fixed relation (e.g. in rigid connection) to any of the positioning system 208, the access port 12, the introducer 210, the tracked pointer 222 and/or other tracked instruments. The fiducial marker(s) 212 may be active or passive markers. A display 206, 2011 may provide an output of the computed data of the navigation system 205. In some examples, the output provided by the display 206, 211 may include axial, sagittal, and coronal views of patient anatomy as part of a multi-view output.

The active or passive fiducial markers 212 may be placed on tools (e.g. the access port 12 and/or the optical imaging system 500) to be tracked, to determine the location and orientation of these tools using the tracking camera 213 and navigation system 205. The markers 212 may be captured by a stereo camera of the tracking system to give identifiable points for tracking the tools. A tracked tool may be defined by a grouping of markers 212, which may define a rigid body to the tracking system. This may in turn be used to determine the position and/or orientation in 3-D of a tracked tool in a virtual space. The position and orientation of the tracked tool in 3-D may be tracked in six degrees of freedom (e.g. x, y, z coordinates and pitch, yaw, roll rotations), in five degrees of freedom (e.g. x, y, z, coordinate and two degrees of free rotation), but preferably tracked in at least three degrees of freedom (e.g. tracking the position of the tip of a tool in at least x, y, z coordinates). In typical use with navigation systems, at least three markers 212 are provided on a tracked tool to define the tool in virtual space; however, it is known to be advantageous for four or more markers 212 to be used.

Camera images capturing the markers 212 may be logged and tracked, by, for example, a closed-circuit television (CCTV) camera. The markers 212 may be selected to enable or assist in segmentation in the captured images. For example, infrared (IR)-reflecting markers and an IR light source from the direction of the camera may be used. In some examples, the spatial position and orientation of the tracked tool and/or the actual and desired position and orientation of the positioning system 208 may be determined by optical detection using a camera. The optical detection may be done using an optical camera, rendering the markers 212 optically visible.

In some examples, the markers 212 (e.g. reflectospheres) may be used in combination with a suitable tracking system, to determine the spatial positioning position of the tracked tools within the operating theatre. Different tools and/or targets may be provided with respect to sets of markers 212 in different configurations. Differentiation of the different tools and/or targets and their corresponding virtual volumes may be possible based on the specification configuration and/or orientation of the different sets of markers 212 relative to one another, enabling each such tool and/or target to have a distinct individual identity within the navigation system 205. The individual identifiers may provide information to the system, such as information relating to the size and/or shape of the tool within the system. The identifier may also provide additional information such as the tool's central point or the tool's central axis, among other information. The virtual tool may also be determinable from a database of tools stored in or provided to the navigation system 205. The markers 212 may be tracked relative to a reference point or reference object in the operating room, such as the patient 202.

In some examples, the markers 212 may include printed or 3-D designs that may be used for detection by an auxiliary camera, such as a wide-field camera (not shown) and/or the optical imaging system 500. Printed markers may also be used as a calibration pattern, for example to provide distance information (e.g. 3-D distance information) to an optical detector. Printed identification markers may include designs such as concentric circles with different ring spacing and/or different types of bar codes, among other designs. In some examples, in addition to or in place of using markers 212, the contours of known objects (e.g. the side of the access port 12) could be captured by and identified using optical imaging devices and the tracking system.

A guide clamp 218 (or more generally a guide) for holding the access port 12 may be provided. The guide clamp 218 may allow the access port 12 to be held at a fixed position and orientation while freeing up the surgeon's hands. An articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g. on another patient support, such as on the surgical bed), to ensure that when locked in place, the guide clamp 218 does not move relative to the patient's head.

In a surgical operating room/theatre, setup of a navigation system may be relatively complicated; there may be many pieces of equipment associated with the surgical procedure, as well as elements of the navigation system 205. Further, setup time typically increases as more equipment is added. To assist in addressing this, the navigation system 205 may include two additional wide-field cameras to enable video overlay information. Video overlay information can then be inserted into displayed images, such as images displayed on one or more of the displays 206, 211. The overlay information may illustrate the physical space where accuracy of the 3-D tracking system (which is typically part of the navigation system) is greater, may illustrate the available range of motion of the positioning system 208 and/or the optical imaging system 500, and/or may help to guide head and/or patient positioning.

The navigation system 205 may provide tools to the neurosurgeon that may help to provide more relevant information to the surgeon, and may assist in improving performance and accuracy of port-based neurosurgical operations. Although described in the present disclosure in the context of port-based neurosurgery (e.g. for removal of brain tumors and/or for treatment of intracranial hemorrhages (ICH)), the navigation system 205 may also be suitable for one or more of: brain biopsy, functional/deep-brain stimulation, catheter/shunt placement (in the brain or elsewhere), open craniotomies, and/or endonasal/skull-based/ear-nose-throat (ENT) procedures, among others. The same navigation system 205 may be used for carrying out any or all of these procedures, with or without modification as appropriate.

In some examples, the tracking camera 213 may be part of any suitable tracking system. In some examples, the tracking camera 213 (and any associated tracking system that uses the tracking camera 213) may be replaced with any suitable tracking system which may or may not use camera-based tracking techniques. For example, a tracking system that does not use the tracking camera 213, such as a radiofrequency tracking system, may be used with the navigation system 205.

Figure 3:
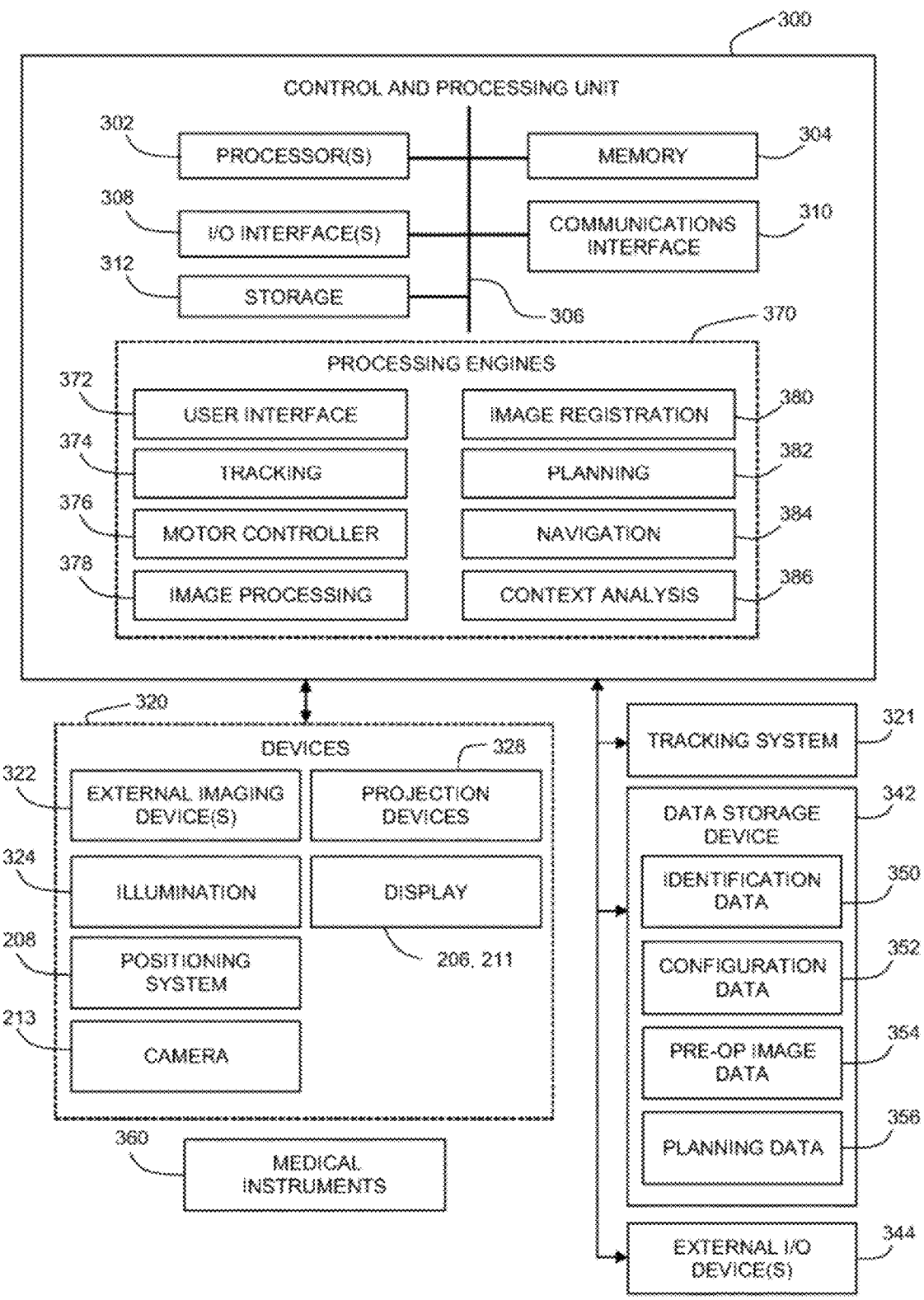
FIG. 3 is a block diagram illustrating an example control and processing system which may be used in the example navigation system of FIGS. 1 and 2.

FIG. 3 is a block diagram illustrating a control and processing system 300 that may be used in the medical navigation system 205 shown in FIG. 2 (e.g. as part of the equipment tower 207). As shown in FIG. 3, the control and processing system 300 may include one or more processors 302, a memory 304, a system bus 306, one or more input/output interfaces 308, a communications interface 310, and storage device 312. The control and processing system 300 may interface with other external devices, such as a tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. The data storage device 342 may also include preoperative image data 354 and/or medical procedure planning data 356. Although the data storage device 342 is shown as a single device in FIG.

3, it will be understood that in other embodiments, the data storage device 342 may be provided as multiple storage devices.

The medical instruments 360 may be identifiable by the control and processing unit 300. The medical instruments 360 may be connected to and controlled by the control and processing unit 300, or the medical instruments 360 may be operated or otherwise employed independent of the control and processing unit 300. The tracking system 321 may be employed to track one or more medical instruments 360 and spatially register the one or more tracked medical instruments to an intraoperative reference frame. For example, the medical instruments 360 may include tracking markers such as tracking spheres that may be recognizable by the tracking camera 213. In one example, the tracking camera 213 may be an infrared (IR) tracking camera. In another example, a sheath placed over a medical instrument 360 may be connected to and controlled by the control and processing unit 300.

The control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, the positioning system 208, the tracking camera 213, one or more projection devices 328, and one or more displays 206, 211.

Exemplary aspects of the disclosure can be implemented via the processor(s) 302 and/or memory 304. For example, the functionalities described herein can be partially implemented via hardware logic in the processor 302 and partially using the instructions stored in the memory 304, as one or more processing modules or engines 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately in FIG. 3, in some examples the processing modules 370 may be stored in the memory 304 and the processing modules 370 may be collectively referred to as processing modules 370. In some examples, two or more modules 370 may be used together to perform a function. Although depicted as separate modules 370, the modules 370 may be embodied as a unified set of computer-readable instructions (e.g. stored in the memory 304) rather than distinct sets of instructions.

Figure 4A:
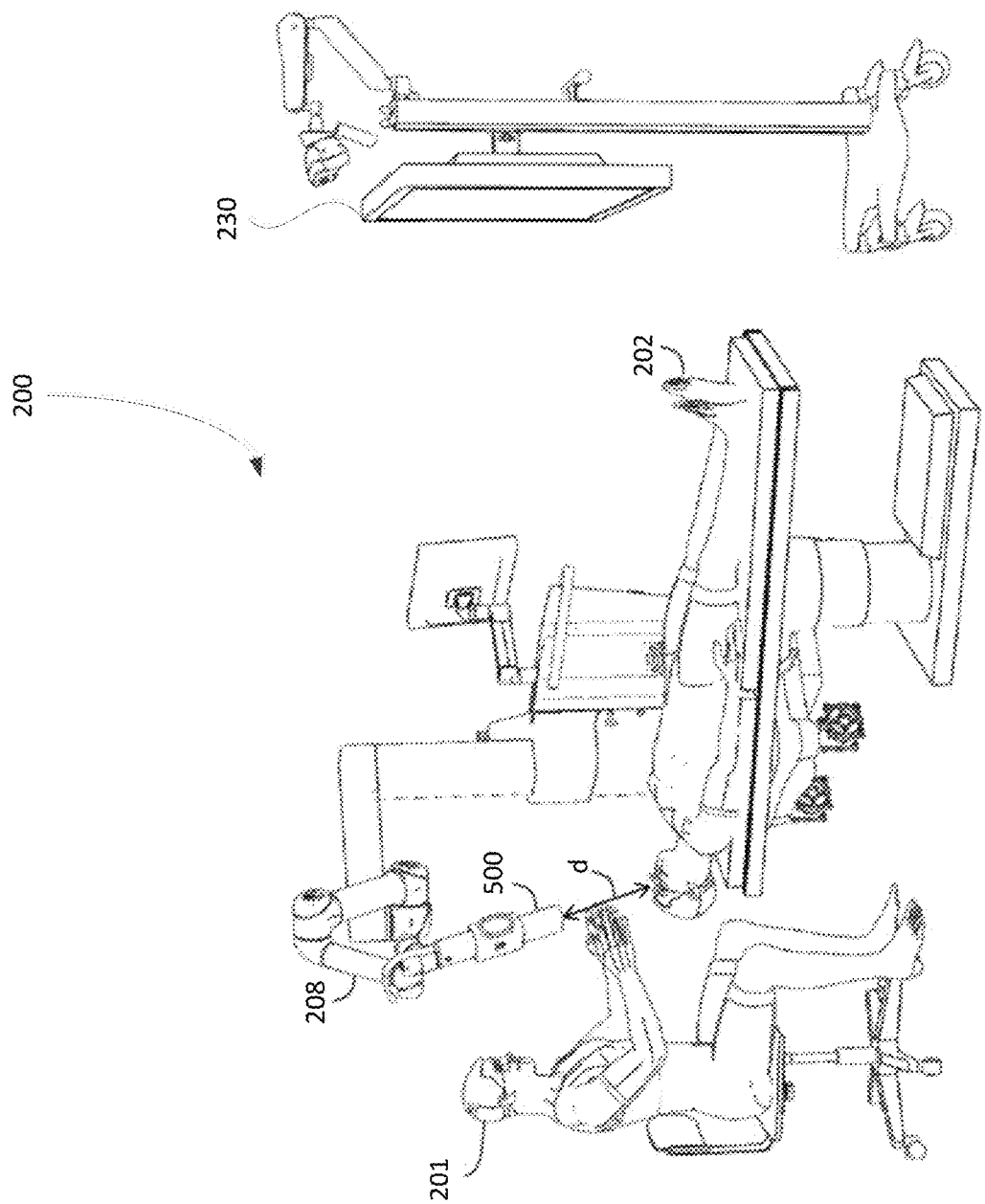
FIG. 4A shows the use of an example optical imaging system during a medical procedure.

FIG. 4A illustrates use of an example optical imaging system 500, described further below, in a medical procedure. Although FIG. 4A shows the optical imaging system 500 being used in the context of a navigation system environment 200 (e.g. using a navigation system as described above), the optical imaging system 500 may also be used outside of a navigation system environment.

An operator, typically a surgeon 201, may use the imaging system 500 to observe the surgical site (e.g. to look down an access port). The optical imaging system 500 may be attached to a positioning system 208, such as a controllable and adjustable robotic arm. The position and orientation of the positioning system 208, imaging system 500, and/or access port may be tracked using a tracking system, such as described for the navigation system 205. The distance between the optical imaging system 500 (more specifically, the aperture of the optical imaging system 500) and the viewing target may be referred to as the working distance. The optical imaging system 500 may be designed to be used in a predefined range of working distance (e.g. in the range of between 15 and 75 centimeters). It should be noted that, if the optical imaging system 500 is mounted on the positioning system 208, the actual available range of working distance may be dependent on both the working distance of the optical imaging system 500 as well as the workspace and kinematics of the positioning system 208. In some embodiments, the optical imaging system 500 may include a manual release button that, when actuated, enables the optical imaging system to be positioned manually. For example, the controller of the optical imaging system 500 may be responsive to manual control input received via a user interface.

Figure 4B:
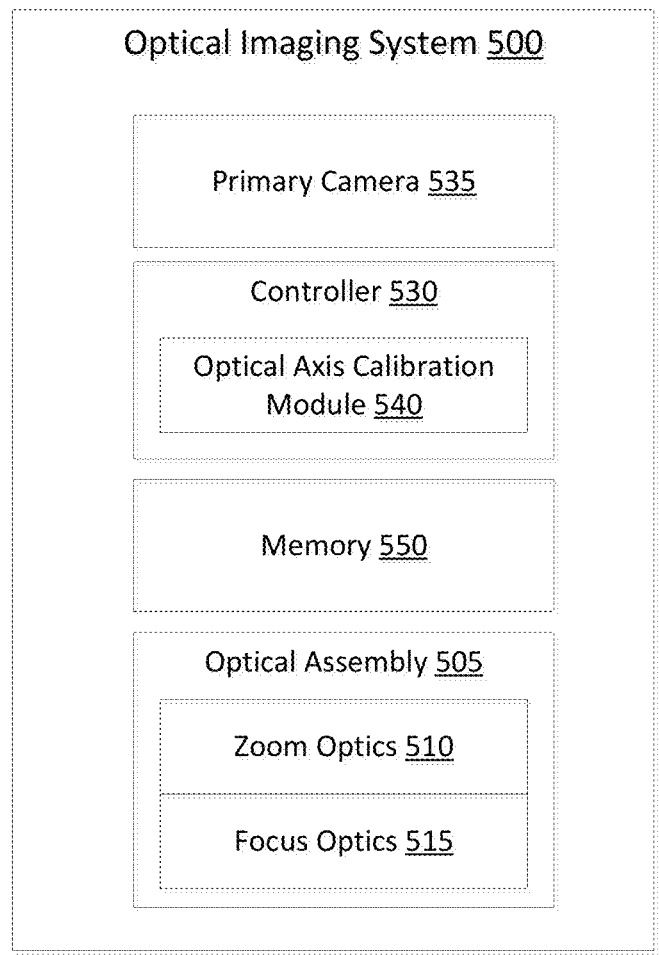
FIG. 4B is a block diagram illustrating components of an example optical imaging system 500.

Reference is now made to FIG. 4B, which shows components of an example optical imaging system 500. The optical imaging system 500 includes a primary camera (or video-scope) 535. The primary camera 535 may be a high-definition (HD) camera that captures image data from the optical assembly. The optical imaging system 500 may also include an optical assembly 505. The optical assembly 505 may include optics (e.g. lenses, optical fibers, etc.) for focusing and zooming on the viewing target. The optical assembly 505 may include zoom optics 510 and focus optics 515. Each of the zoom optics 510 and focus optics 515 are independently moveable within the optical assembly, in order to adjust the zoom and focus, respectively. The optical assembly 505 may include an aperture which may be adjustable.

The optical imaging system 500 also includes a memory 550 and a controller 530 coupled to the memory 550. The controller 530 may comprise one or more processors (e.g. micro-processors), programmable logic devices (e.g. field-programmable gate arrays, or FPGAs), application-specific integrated circuits (ASICs), or combinations thereof. In at least some embodiments, the controller 530 is configured to control operation of a zoom actuator and a focus actuator. The controller 530 may receive control input indicating a desired zoom and/or focus and, in response to receiving the input, the controller 530 may cause the zoom actuator and/or the focus actuator to move the zoom optics 510 and focus optics 515, respectively.

The controller 530 is also configured to control operation of the primary camera 535. The primary camera 535 may output camera data to the controller 530, which in turn transmits the data to an external system for viewing. The captured images can then be viewed on larger displays and may be displayed together with other relevant information, such as a wide-field view of the surgical site, navigation markers, etc.

As shown in FIG. 4B, the controller 530 may also include an optical axis calibration module 540. The optical axis calibration module 540 may perform operations for determining an orientation of the primary camera 535 relative to an axis of rotation of the positioning system 208. The optical axis calibration module 540 may be configured to carry out the calibration automatically or upon receipt of a user input or request to calibrate. In some embodiments, the optical axis calibration module 540 may be communicably connected to a positioning mechanism that is used to control position and orientation (e.g. lateral, rotational, etc.) of the optical imaging system 500 and parts thereof (such as optical assemblies 505). For example, the optical axis calibration module 540 may instruct a controller for the positioning mechanism to initiate rotational movement of the mechanical arm which supports the optical imaging system 500.

In at least some embodiments, the primary camera 535, optical assembly 505 (including the zoom optics 510 and focus optics 515), controller 530, and memory 550 may all be housed within a single housing of the optical imaging system 500. The housing may be provided with a frame on which trackable markers may be mounted to enable tracking by a navigation system. The optical imaging system 500 may be mountable on a moveable support structure, such as a positioning system (e.g. robotic arm) of a navigation system, a manually operated support arm, a ceiling-mounted support, a moveable frame, or other support structure. In some embodiments, the optical imaging system 500 may include a support connector, such as a mechanical coupling, to enable the optical imaging system 500 to be mounted to and dismounted from the support structure.

Figure 5:
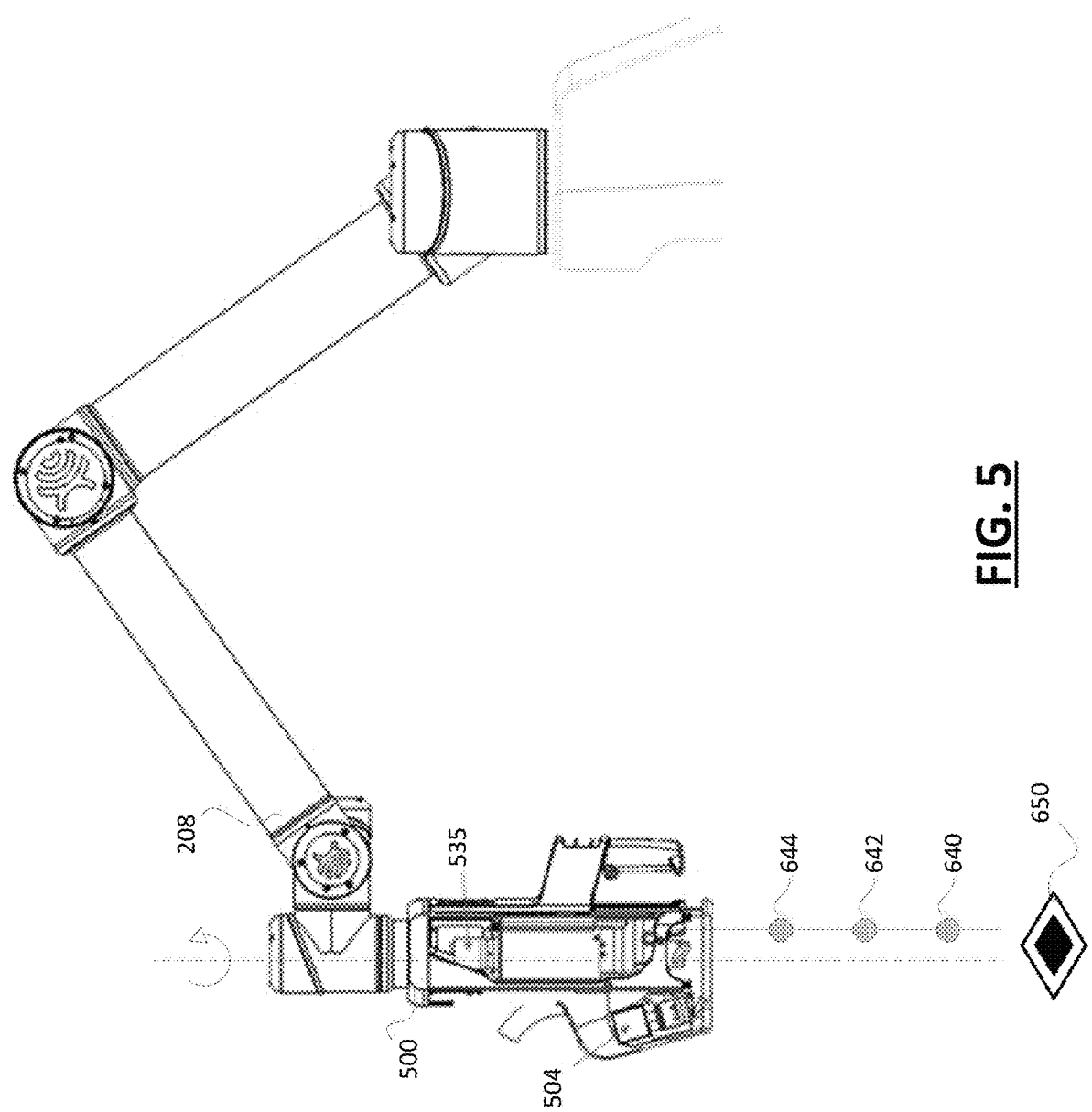
FIG. 5 is a partial side cross-sectional view of the augmented optical imaging system mounted on a positioning system.

The disclosed methods for optical axis calibration are described with reference to FIGS. 5 to 8. FIG. 5 shows the optical imaging system 500 mounted to a positioning system 208 (e.g. a robotic arm) of a medical navigation system. The optical imaging system 500 is shown with a housing that encloses the zoom and focus optics, the primary camera 535, and a secondary camera 504. FIG. 5 shows the secondary camera 504 being angled with respect to the primary camera 535. In particular, the primary camera 535 is positioned substantially vertically within the housing of the augmented optical imaging system while the secondary camera 504 is positioned at an angle with respect to the vertical.

While FIG. 5 illustrates one example embodiment of a system which may implement the disclosed calibration methods of the present application, it will be understood that said methods may apply more generally to any imaging system that includes one or more cameras mounted on a movable structure and which are used for imaging a target.

Previous techniques of calibration relied on tracking information of the medical navigation system, which may contain and accumulate error. The disclosed methods of the present application enable calibration without use of tracking information. More specifically, a calibration method is proposed which uses data from a video stream from an optical imaging system of a medical navigation system. Video data of a target marker is captured, the target marker including unique detectable features. Based on the captured video data, a transform is computed to compensate for misalignment of the optical axis of the camera. Once the optical axis calibration is completed, the camera's view may rotate around a single point. In particular, when the positioning apparatus (e.g. mechanical arm) is in rotation mode and the optics are set to a certain magnification level, the camera's view may rotate around a single point where the center of said rotation is less than or equal to a fixed distance from the center of the screen. Beyond rotation, this calibration may enable the alignment of the optical axis to ensure that the optics are centered on a particular target point and oriented to align along a desired axis.

Figure 6:
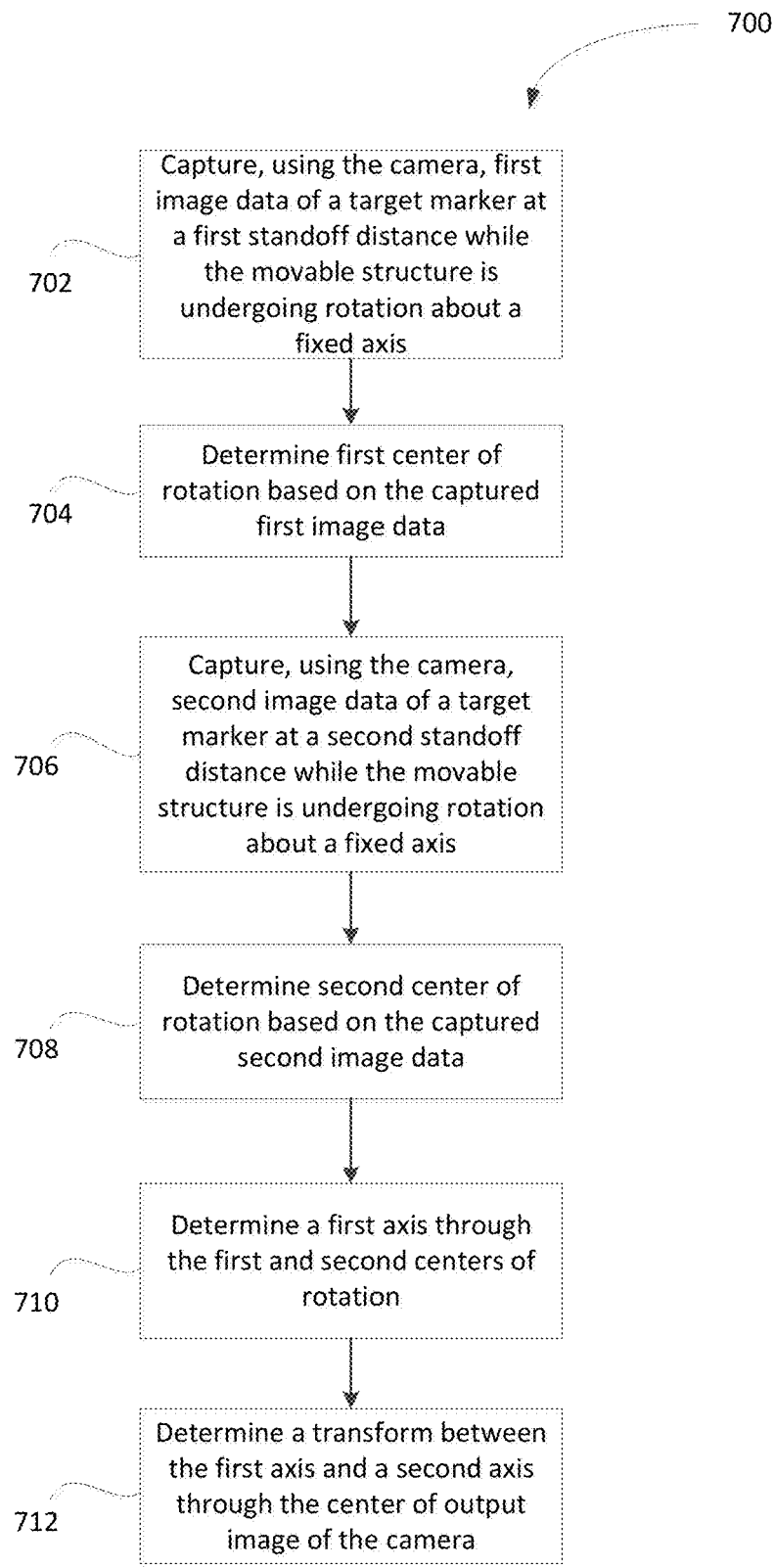
FIG. 6 shows, in flowchart form, an example method of generating a stereoscopic image of a target using the augmented optical imaging system of FIG. 4B.

An example method 700 for calibrating an optical axis of a camera that is mounted to a movable structure is shown in FIG. 6. The method 700 may be implemented in a digital microscope system. For example, the method 700 may be implemented by a controller of an optical imaging system integrated into a digital microscope, or similar processing unit for controlling operations of cameras of an optical imaging system.

Figure 7:
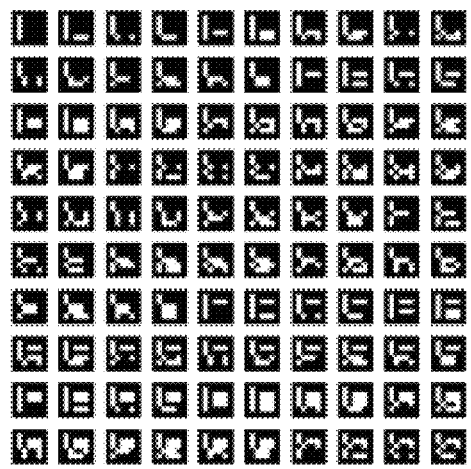
FIG. 7 shows an example of a target marker.

In operation 702, the controller captures, using the camera, first image data of a target marker at a first standoff distance while the movable structure is undergoing rotation about a fixed axis. The first standoff distance may, for example, be 25 centimeters. An example target marker 650 is shown in FIG. 5. The target marker is a grid of squares each including unique detectable features. In some embodiments, the target marker may be an ArUco marker, as shown in the example of FIG. 7. An ArUco marker is a synthetic square marker composed by a wide black border and an inner binary matrix which determines its identifier. The black border facilitates fast detection in the image and the binary codification allows its identification and the application of error detection and correction techniques. The movable structure may, for example, be a robotic arm that is part of a medical navigation system. The robotic arm may support the camera and be configured to rotate about a fixed wrist joint, or a vertical axis.

Figure 8:
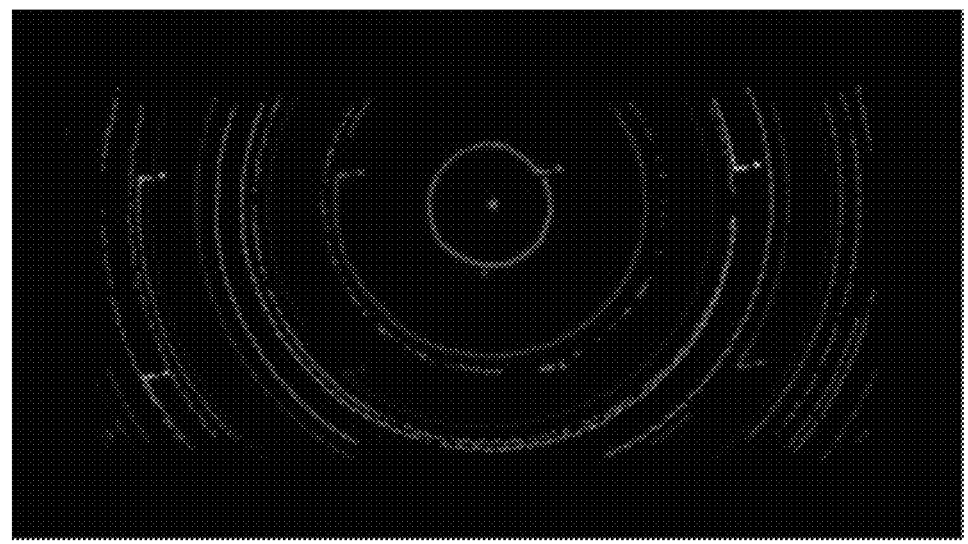
FIG. 8 shows a series of colored traces generated from video capture of a target marker during rotation of a camera about a fixed axis.

In at least some embodiments, the first image data comprises video of the target marker. That is, as the movable structure rotates about a fixed axis, video data of the target marker is recorded. The video may be processed to identify unique identifiers (IDs) associated with the different features of the grid squares. The controller identifies patterns marked by the unique IDs in the video frames as a result of rotation of the movable structure. For example, as the squares of the Aruco marker move in a captured video of the marker, the unique IDs are marked at each frame of the captured video. Each ID mark may form a circle during the rotation. As shown in FIG. 8, the circles may be displayed as a series of colored traces in an image generated based on the video capture. In particular, the patterns comprise a plurality of concentric tracking circles marked by the unique IDs.

In operation 704, a first center of rotation is determined based on the captured first image data. In particular, the first center of rotation may be the point corresponding to the center of the concentric tracking circles marked by the IDs associated with features of the grid squares.

In operation 706, the controller captures second image data of the target marker at a second standoff distance while the movable structure undergoes rotation about the fixed rotational (e.g. vertical) axis. The second standoff distance may, for example, be 40 centimeters. In operation 708, the controller determines a second center of rotation based on the captured second image data. The second center of rotation may be determined in a manner similar to operation 704. That is, the second center of rotation may be a point corresponding to a center of concentric tracking circles marked by IDs associated with features of the grid squares in the video captured during rotation of the movable structure.

The operation of capturing image data of the target marker can be performed for rotations at various standoff distances along a working distance to generate a data set of centers of rotation along the fixed rotational axis. In particular, the rotations can be performed at more than two different working distances. For example, a data set of centers of rotations may be generated from rotations of the movable structure at three different standoff distances, as shown in FIG. 5 (represented by 640, 642 and 644). The standoff distances may, in some embodiments, may be selected from a range between 25 and 55 centimeters. For example, the selected standoff distances may be 25, 40 and 55 centimeters.

More generally, a data set of rotation centers may be generated from a range of standoff distance values. In some embodiments, the standoff distances that are selected for use in the calibration process may depend on the focal lengths of the optics (i.e. camera lens) employed by the optical imaging system. For example, the selected standoff distances may include three values, with the smallest selected distance corresponding to a minimum focal length (or a value slightly greater than the minimum focal length) for the primary camera (lens), the largest selected distance corresponding to a maximum focal length (or a value slightly less than the maximum focal length) for the primary camera, and a value that is between the selected smallest and largest distances (i.e. greater than the smallest selected distance and less than the largest selected distance).

A line that goes through all of these data points (i.e. rotation centers) may be considered as the current optical axis. In operation 710, a first axis which goes through the centers of rotation is determined by the controller. If this first axis does not coincide with a second axis through the centers of the camera screen at the various standoff distances, it may be determined that the center of rotation is off-center. The second axis may, in some embodiments, be fixed prior to the rotations. The calibration method 700 is designed to center the rotation. This may be done by applying a transform between the first axis and the second axis. In operation 712, the controller computes a transform from the first axis to the second axis. For example, a matrix representing an affine transform which maps one set of 3-D coordinates (corresponding to one of the first and second axes) to another set of 3-D coordinates (corresponding to the other of the first and second axes) may be determined in operation 712.

In some embodiments, the disclosed method may also include validating the calibration of the optical axis. For example, the validation may be done by performing a rotation of the movable structure about the determined first axis at a standoff distance which is different from the standoff distances used during the calibration ("calibration standoff distances"). The rotation may, for example, be performed at a middle point between two of the calibration standoff distances. The calibration may be determined to be successful if the center of the optical axis rotation is sufficiently close to the center of the camera screen. Specifically, if a distance between the center of the optical axis rotation and the center of the camera screen is less than a threshold, the calibration may be validated as successful. The threshold may, for example, be specified in pixels. In this way, the validation operation may provide confirmation of whether, when the movable structure is in rotation mode, the camera's view rotates around a single point at the center of the screen, accurate to within a circle of predetermined radius (in pixels).

The various embodiments presented above are merely examples and are in no way meant to limit the scope of this application. Variations of the innovations described herein will be apparent to persons of ordinary skill in the art, such variations being within the intended scope of the present application. In particular, features from one or more of the above-described example embodiments may be selected to create alternative example embodiments including a sub-combination of features which may not be explicitly described above. In addition, features from one or more of the above-described example embodiments may be selected and combined to create alternative example embodiments including a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for calibrating an optical axis of a camera mounted to a movable structure, the method comprising:
   for each of two or more standoff distances for the camera:
      capture, using the camera, video data of a target marker while the movable structure is undergoing rotation about a fixed axis, the target marker being a grid of squares each including unique detectable features;
      process the video data to identify unique identifiers associated with features of the grid squares;
      identify a plurality of concentric tracking circles marked by the unique identifiers in the video frames as a result of rotation of the movable structure; and
      determine a respective center of rotation based on the captured video data, the center of rotation being a center of the plurality of concentric tracking circles;
   determine a first axis which goes through the centers of rotation;
   determine a transform between the first axis and a second axis through the center of the camera screen; and
   validating the calibration, wherein the validation is done by performing a rotation of the movable structure about the determined first axis at a standoff distance that is different from the two or more standoff distances and determining whether a distance between the center of rotation and the center of the camera screen is less than a threshold.

2. The method of claim 1, wherein the movable structure is a robotic arm, and wherein the robotic arm is rotatable about a fixed wrist joint.

3. The method of claim 1, wherein the two or more standoff distances are selected based on minimum and maximum focal lengths of optics of the camera.

4. The method of claim 1, wherein the two or more standoff distances are selected from a range between 25 centimeters to 55 centimeters.

5. The method of claim 1, wherein the validation further comprises measuring the distance in pixels between the center of the camera screen and the center of optical axis rotation.

6. The method of claim 1, wherein the target marker comprises an Aruco marker.

7. An optical imaging system for imaging a target during a medical procedure, the system comprising:
   a movable arm;
   a camera mounted on the movable arm, the camera capturing a first image of the target; and
   a processing unit for calibrating the camera, the processing unit being configured to:
      for each of two or more standoff distances for the camera:
         capture, using the camera, video data of a target marker while the movable arm is undergoing rotation about a fixed axis, the target marker being a grid of squares each including unique detectable features;
         process the video data to identify unique identifiers associated with features of the grid squares;
         identify a plurality of concentric tracking circles marked by the unique identifiers in the video frames as a result of rotation of the movable structure; and
         determine a respective center of rotation based on the captured video data, the center of rotation being a center of the plurality of concentric tracking circles;
      determine a first axis which goes through the centers of rotation;
      determine a transform between the first axis and a second axis through the center of the camera screen; and
      validate the calibration, wherein the validation is done by performing a rotation of the movable arm about the determined first axis at a standoff distance that is different from the two or more standoff distances and determining whether a distance between the center of rotation and the center of the camera screen is less than a threshold.

8. The optical imaging system of claim 7, wherein the movable arm is a robotic arm, and wherein the robotic arm is rotatable about a fixed wrist joint.

9. The optical imaging system of claim 7, wherein the two or more standoff distances are selected based on minimum and maximum focal lengths of optics of the camera.

10. The optical imaging system of claim 7, wherein the two or more standoff distances are selected from a range between 25 centimeters to 55 centimeters.

11. The optical imaging system of claim 7, wherein the validation further comprises measuring the distance in pixels between the center of the camera screen and the center of optical axis rotation.

12. The optical imaging system of claim 7, wherein the target marker comprises an Aruco marker.

* * * * *